United States Patent [19]

Modglin

[11] Patent Number: 4,508,110

[45] Date of Patent: Apr. 2, 1985

[54] BODY JACKET

[76] Inventor: Michael D. Modglin, 3229 Timberline, Winter Haven, Fla. 33881

[21] Appl. No.: 531,847

[22] Filed: Sep. 14, 1983

[51] Int. Cl.³ .................................................. A61F 5/02
[52] U.S. Cl. ......................................... 128/78; 128/90; 128/545; 2/44
[58] Field of Search ................. 128/78, 543, 545, 546, 128/90; 2/44, 2, 2.5, 218; 24/117, 119

[56] References Cited

U.S. PATENT DOCUMENTS 2,053,600 9/1936 Camp ............................... 128/543 X
2,163,463 6/1939 Kennedy ...................................... 2/2

FOREIGN PATENT DOCUMENTS 550539 12/1957 Canada ................................... 128/78

*Primary Examiner*—Richard J. Apley
*Assistant Examiner*—Alan W. Cannon
*Attorney, Agent, or Firm*—Duckworth, Allen, Dyer & Pettis

[57] ABSTRACT

A rigid body jacket having an anterior section and a posterior section. The two sections are joined by corset-type lacings with a pair of bilateral panels laced to the posterior section and attached to the anterior panels by snaps. The lacings are terminated in buckles and straps, the straps being faced with Velcro ® type fastener material. Mating Velcro ® material strips are cemented to the anterior section. The two sections are fitted to the patient, and the laces cut and spliced to a desired tightness with the straps attached to the Velcro ® strips. The jacket thereafter may be easily removed and put back on by the patient without assistance.

8 Claims, 4 Drawing Figures

BODY JACKET

BACKGROUND OF THE INVENTION

1. Field of the Invention

The present invention relates to body jacket type orthoses for limiting motion in thoracic or lumbosacral areas, and more particularly to a rigid orthosis which can be easily donned and doffed by the elderly and the handicapped.

2. Description of the Prior Art

Although body jackets have been known and used for many years in the treatment and rehabilitation of the spine, elderly, injured, and handicapped persons have experienced difficulty in putting on rigid orthoses, generally requiring assistance. It is known to use corset lacings and corset buckles in combination with soft, flexible orthoses to provide even adjustment and an easy release. For example, the buckle taught by Camp in U.S. Pat. No. 2,053,600 has improved the adjustment of non-rigid orthoses. Using the Camp buckle, corset lacings threaded through the buckle are adjusted with the orthosis on the patient. The buckle straps are attached to the orthosis with snaps, permitting ease of removal and reinstallation. However, when buckles and snaps are applied to a rigid orthosis, it is found that the snaps do not hold due to the rigidity of the material.

One attempt of this approach is the Raney Flexion Jacket ®. Corset lacing on one side secures the anterior section to the posterior section and once adjusted, is permanently fixed. The other side is attached by two straps, resulting in a body jacket that is difficult to put on. When the straps are tightened, the opposing side may rotate or twist toward the last adjusted strap. For many patients, this design requires two people to properly position the orthosis. Thus, many elderly and handicapped patients are unable to don the jacket.

A rigid body jacket is disclosed in U.S. Pat. No. 4,202,327 having a number of straps for connecting right and left sections with the straps secured to the jacket with Velcro ® strips. The necessity for adjusting straps both front and rear prevents use by many patients without assistance in doffing and donning the orthosis.

Thus, there is a long felt need for a body jacket type rigid orthosis which can be adjusted on the patient and then easily removed and replaced by the patient without disturbing the adjustment.

SUMMARY OF THE INVENTION

My invention is a rigid body jacket having an anterior section and a posterior section. The posterior section includes a pair of bilateral panels laced to it with corset-type lacings. The panels have a set of female snaps which connect with male snaps on the anterior section. The lacings terminate on each side in two Camp-type buckles and fixed straps. The straps are lined with Velcro ® hook fastener material. Strips of mating loop Velcro ® are cemented to the anterior section.

The orthosis is initially installed on the patient by attaching the panels to the anterior section by the snaps and attaching the straps to the appropriate Velcro ® strips or pads. The lacings are tightened until the orthosis is in its proper position. The lacings are cut and spliced so as to form a continuous loop.

As may be recognized, the patient may remove the orthosis by pulling the straps from the Velcro ®, and permitting the laces to loosen between the anterior and posterior sections. He then unsnaps the panels, permitting removal of the two sections. When putting the body jacket on, the patient first snaps the panels in place and then pulls the lacing snug by means of the straps, securing the straps to the Velcro ® pads.

Many materials are known that are suitable for the outer shell of the body jacket of my invention, although I prefer polyethylene. The anterior and posterior sections may be lined with Aliplast ® or Pelite ® or other closed cell polyethylene foam for comfort of the wearer.

It is therefore a principal object of my invention to provide a rigid orthosis capable of being donned and doffed by the patient without assistance.

It is another object of my invention to provide a body jacket orthosis having a pair of detachable side panels laced to the posterior section by corset-type lacing.

It is yet another object of my invention to provide a rigid orthosis having Velcro ® attached straps for tightening the lacings.

It is a further object of my invention to provide a rigid body jacket that may be removed and replaced without affecting the adjustment of the orthosis.

These and other objects and advantages will become apparent from the following detailed description when read in conjunction with the drawings.

DETAILED DESCRIPTION OF THE PREFERRED EMBODIMENT

Figure 1:
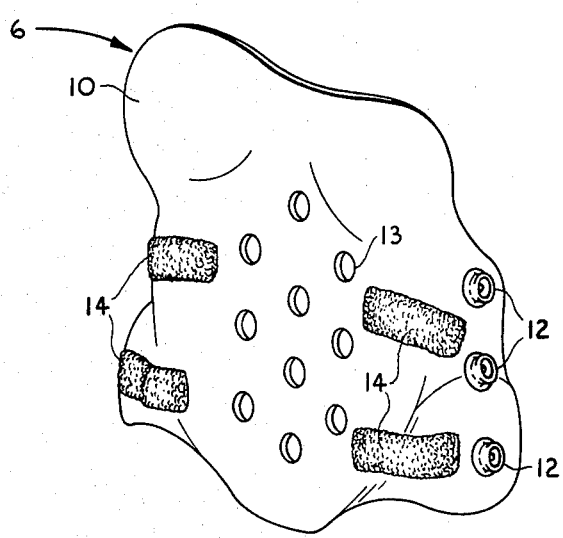
FIG. 1 is a perspective view of the anterior section of the orthosis of my invention.

My invention is a rigid body jacket type orthosis which may be easily donned and removed from the patient, commonly without assistance. Referring first to FIG. 1, an anterior section 6 of the body jacket is shown which includes a rigid plastic shell 10 molded to fit the patient. As is well known in this type of orthosis, the shell is formed to fit the patient and to provide the required control of the patient's body. Although I do not limit my invention to the type shown, the anterior section shown in FIG. 1 extends from the hip area to the upper chest area. A series of ventilation openings 13 may be provided through the shell 10. Four strips or pads 14 of Velcro ® loop type material are cemented to the shell 10 as shown. Male snap buttons 12 are disposed on each lateral edge of shell 10 with the snaps 12 on the left side visible in FIG. 1.

Figure 2:
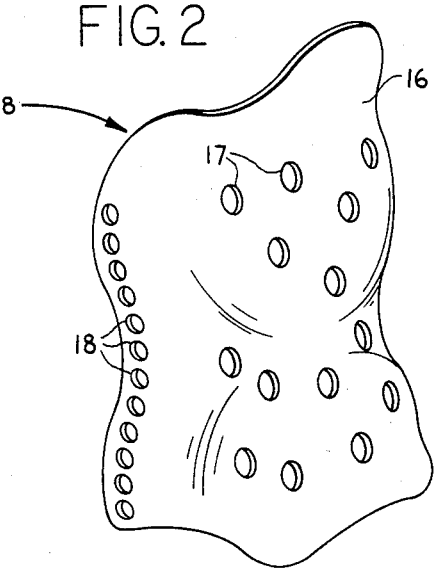
FIG. 2 is a perspective view of the posterior section of the orthosis of my invention.

Posterior section 8 of my body jacket is shown in FIG. 2 having plastic shell 16. Shell 16 is also molded to conform to the patient's back area and to provide the desired physical corrections. Ventilation openings 17 may be provided as desired. Along each lateral edge of shell 16, a series of lacing holes 18 is provided. Although the number of lacing holes 18 is a design parameter, I have found that twelve holes is preferable in accordance with my invention.

A number of suitable materials is known in the art for forming shells 10 and 16. I have found that polyethylene is eminently suitable, although other materials such as polypropylene, Orthoplast®, and Kydex® are suitable. Although not shown in FIGS. 1 and 2, shells 10 and 16 are lined with a soft compressible material such as Aliplast® or Pelite® for the comfort of the patient. As will be understood, other foam-type plastics are suitable for lining.

Figure 3:
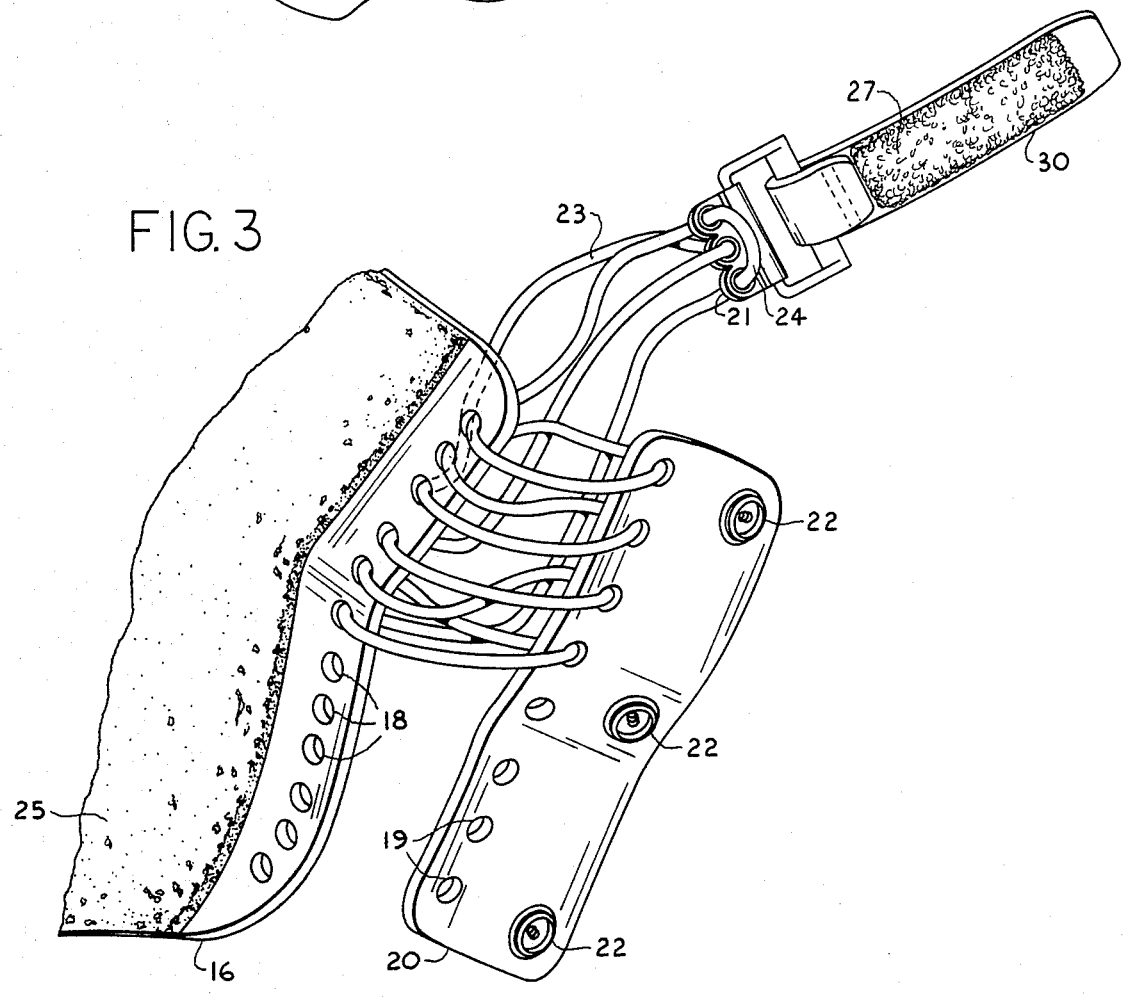
FIG. 3 is an anterior view of part of the posterior section of FIG. 2 with one set of laces attached to a lateral panel.

To joint the anterior section 6 and the posterior section 8, I provide the closure shown partially in FIG. 3. A partial view of the interior surface of shell 16 is shown having twelve lacing holes 18 along the left edge thereof. Also, the resilient backing material 25 is seen in partial view which extends short of lacing holes 18. A lateral panel 20 which may also be formed from plastic is provided which is bent to match the curvature of the sides of the anterior shell 10 of FIG. 1. A set of female snap buttons 22 is installed in the forward edge of lateral panel 20, with panel 20 shaped such that female snap buttons 22 will engage male snap buttons 12 on interior section 6.

Lateral panel 20 is provided with eight lacing holes and is connected to posterior shell 16 by two continuous laces 23, with only one lace shown in FIG. 3 for clarity. It is therefore to be understood that a second lace 23 is installed in the lower sets of lacing holes 18 and 19. Lacing 23 is connected to corset buckle 21 which may be of the type shown in the Camp patent. As may be noted, the ends of lacing 23 are joined at the buckle by joint 24 forming a continuous loop. I prefer to use a nylon cord which is somewhat resilient and extremely strong for lacing 23. Joint 24 can be made by chemical or heat bonding means to form the desired continuous loop. Buckle 21 is attached to a short strap 30 lined with Velcro® hook material 27 of the type to mate with Velcro® loop pads 14 on shell 10.

When the orthosis is first fitted to the patient, the anterior and posterior sections 6 and 8 are placed on the patient, the lateral panels 20 are snapped in place, and the straps 30 are attached appropriately to Velcro® pads 14. The technician then tightens the lacings 23 to the desired tension, marking the length of each. The orthosis may then be removed and the ends of lacings bonded to form connection 24 at each buckle 21. As may be understood, the orthosis is then permanently adjusted with respect to the orientation of the anterior and posterior sections 6 and 8 and cannot be disturbed by removing and putting on the orthosis.

Figure 4:
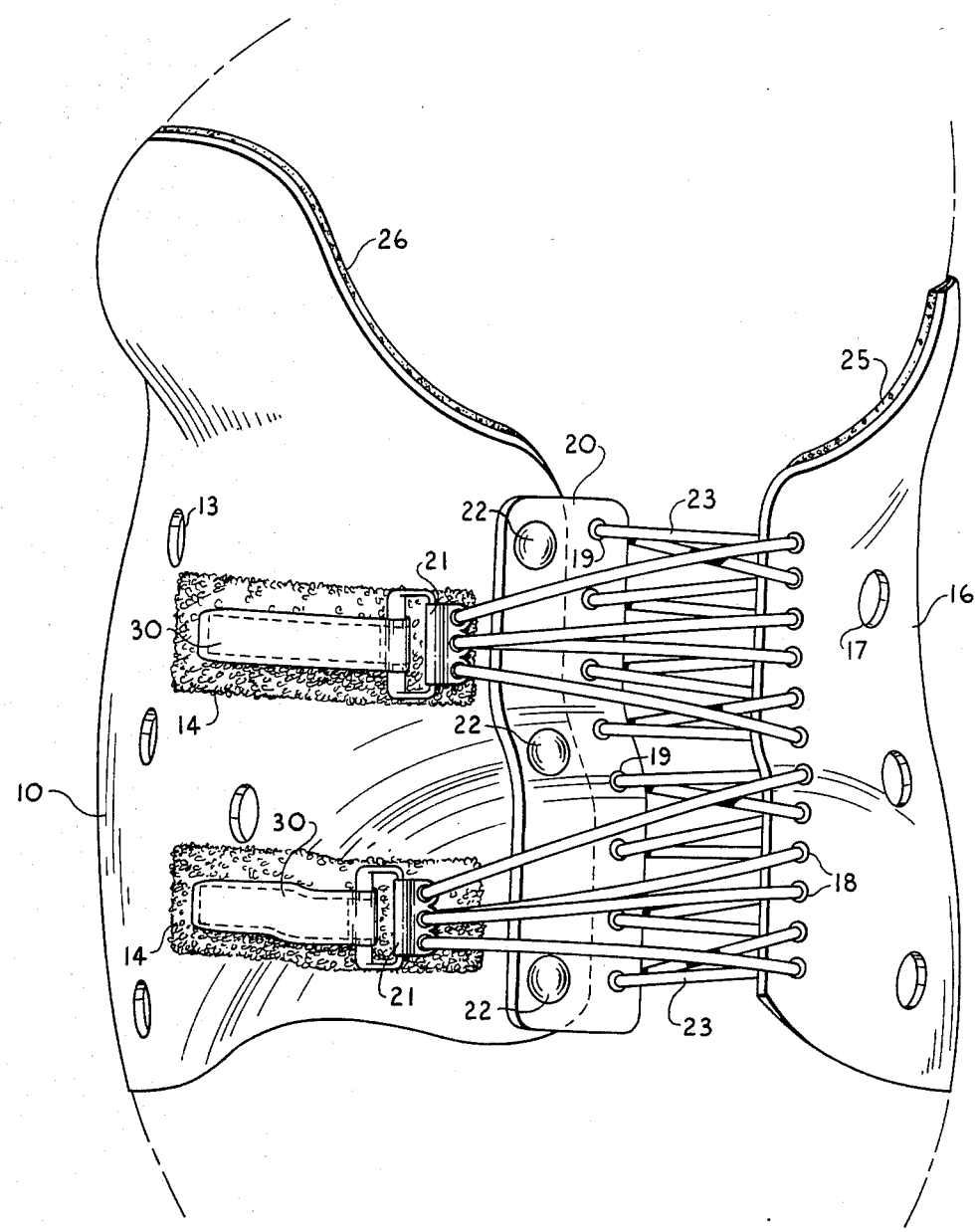
FIG. 4 is a side view of the orthosis of my invention showing a lateral panel attached to the anterior section and laced to the posterior section.

Turning now to FIG. 4, the body jacket in its installed condition is shown. Anterior portion 10 having resilient lining 26 is seen to have left lateral panel 20 snapped to its left lateral edge. Each strap 30 has been pulled to snug the respective lacings 23 and pressed onto Velcro® pads 14 to secure straps 30 to anterior section 10. It will be noted that the lacings attached to buckles 21 pass over lateral panels 20, locking panels 20 in place. As seen in FIG. 3, backing or lining material 25 does not extend to the lateral edges of anterior shell 16. Therefore, clearance is provided for lacings 23 such that lacings 23 do not press into the patient's side.

When a patient desires to remove the body jacket, he simply releases the four straps 30 which are within easy reach. This action loosens the lacings, permitting the patient to unsnap one or both lateral panels 20 and to remove the entire jacket. When the patient wishes to put the jacket on, he can easily snap the lateral panels in place, draw up one set of lacings 23 by pulling on strap 30, and thereafter press strap 30 onto the appropriate Velcro® pad 14. At that point the other set of lacings is snugged up and strap 30 fastened to pad 14. Advantageously, the corset lacing permits this adjustment without skewing of the shells and permits easy adjustment of tension without necessity of the patient attempting to thread straps through buckles or other adjustments common in prior art orthoses.

I have herein disclosed a novel rigid body jacket having an anterior section and a posterior section in which the two sections are coupled together by corset lacings attached to removable lateral panels. This permits many elderly or handicapped patients, who otherwise would need assistance, to don and doff the body jacket without aid. Although I have disclosed a particular design, it will be understood that those of skill in the art may make many modifications, changes in materials, and the like without departing from the spirit and scope of my invention.

I claim:

1. A rigid orthosis for limiting motion in the thoracic or lumbosacral areas of a human patient which can be easily donned and doffed by the patient comprising:

a substantially rigid body jacket having a patient-fitting anterior section, the lateral edges of which terminate in the left and right anterolateral regions of the torso and a patient-fitting posterior section, the lateral edges of which terminate in the left and right posterolateral regions of the torso in spaced, opposing relationship to said anterior section lateral edges a pair of elongate panels, each having attachment means for selectively removably attaching one of said panels to each of the lateral edges of said anterior section;

lacing means for connecting each of said panels to a lateral edge of said posterior section; and adjusting and attaching means for directly securing said lacing means to said anterior section during donning of said orthosis.

2. The orthosis as defined in claim 1 in which said attachment means includes female snaps attached to said panels and male snaps attached to said lateral edges of said anterior section.

3. The orthosis as defined in claim 1 in which said lacing means includes:

a set of lacing holes along each lateral edge of said posterior section;

a set of lacing holes along a lateral edge of each of said panels;

first laces laced between said set of said lacing holes in one panel and said set of lacing holes in one lateral edge of said posterior section, said first laces terminating in first buckles and straps; and second laces laced between said set of said lacing holes in the other panel and said set of lacing holes in the other lateral edge of said posterior section, said second laces terminating in second buckles and straps.

4. The orthosis as defined in claim 3 in which said adjusting and attaching means includes:

first hook and loop fastening material attached to said straps; and second hook and loop fastening material mating with said first fastening material attached to said anterior section.

5. The orthosis as defined in claim 1 in which said anterior section and said posterior section are lined with soft compressible material.

6. The orthosis as defined in claim 2 in which said anterior section and said posterior section are formed of polyethylene.

7. The orthosis as defined in claim 3 in which said first and second laces each comprise two continuous laces, each of said continuous laces connected to a separate one of said buckles and snaps, the lengths of said continuous laces initially adjusted on the patient to provide a desired tension between said anterior and posterior portions.

8. The orthosis as defined in claim 4 including means for locking said panels in place, said means comprising said laces in a tightened condition crossing over said panels and secured to said anterior section by means of said first hook and loop fastening material coupled to said second hook and loop material.

* * * * *